(12) United States Patent
Stewart et al.

(10) Patent No.: US 8,586,069 B2
(45) Date of Patent: *Nov. 19, 2013

(54) ANTI-PROLIFERATIVE AND ANTI-INFLAMMATORY AGENT COMBINATION FOR TREATMENT OF VASCULAR DISORDERS

(75) Inventors: Gordon Stewart, San Francisco, CA (US); Gina Zhang, Fremont, CA (US); Nancy Kirsten, San Carlos, CA (US); Paul Consigny, San Jose, CA (US); Stephen Dugan, San Francisco, CA (US); Gene Park, Oakland, CA (US); Christopher Feezor, San Jose, CA (US); Wouter Roorda, Palo Alto, CA (US); Syed Faiyaz Ahmed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 734 days.

This patent is subject to a terminal disclaimer.

(21) Appl. No.: 11/322,282

(22) Filed: Dec. 29, 2005

(65) Prior Publication Data

US 2006/0105019 A1    May 18, 2006

Related U.S. Application Data

(63) Continuation of application No. 10/882,506, filed on Jun. 30, 2004, now abandoned, and a continuation-in-part of application No. 11/089,763, filed on Mar. 25, 2005, now abandoned, which is a continuation-in-part of application No. 10/320,935, filed on Dec. 16, 2002, now Pat. No. 6,908,624.

(51) Int. Cl.
*A61F 13/00* (2006.01)
*A61F 2/00* (2006.01)

(52) U.S. Cl.
USPC .......................................... 424/422; 424/423

(58) Field of Classification Search
None
See application file for complete search history.

(56) References Cited

U.S. PATENT DOCUMENTS

| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |

(Continued)

FOREIGN PATENT DOCUMENTS

| DE | 42 24 401 | 1/1994 |
| EP | 0 301 856 | 2/1989 |

(Continued)

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

(Continued)

*Primary Examiner* — Carlos Azpuru
*Assistant Examiner* — Casey Hagopian
(74) *Attorney, Agent, or Firm* — Squire Sanders (US) LLP

(57) ABSTRACT

Drug-delivery systems such as drug-delivery stents having an anti-proliferative agent such as everolimus and an anti-flammatory agent such as clobetasol are provided. Also disclosed are methods of treating a vascular impairment such as restenosis or vulnerable plaque.

9 Claims, 1 Drawing Sheet

(56) References Cited

U.S. PATENT DOCUMENTS

| | | | |
|---|---|---|---|
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |
| 5,516,881 A | 5/1996 | Lee et al. | |
| 5,540,931 A * | 7/1996 | Hewitt et al. | 424/434 |
| 5,569,463 A | 10/1996 | Helmus et al. | |
| 5,578,073 A | 11/1996 | Haimovich et al. | |
| 5,584,877 A | 12/1996 | Miyake et al. | |
| 5,605,696 A * | 2/1997 | Eury et al. | 424/423 |
| 5,607,467 A | 3/1997 | Froix | |
| 5,609,629 A | 3/1997 | Fearnot et al. | |
| 5,610,241 A | 3/1997 | Lee et al. | |
| 5,616,338 A | 4/1997 | Fox, Jr. et al. | |
| 5,624,411 A | 4/1997 | Tuch | |
| 5,628,730 A | 5/1997 | Shapland et al. | |
| 5,644,020 A | 7/1997 | Timmermann et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,674,242 A | 10/1997 | Phan et al. | |
| 5,679,400 A | 10/1997 | Tuch | |
| 5,700,286 A | 12/1997 | Tartaglia et al. | |
| 5,702,754 A | 12/1997 | Zhong | |
| 5,711,958 A | 1/1998 | Cohn et al. | |
| 5,716,981 A | 2/1998 | Hunter et al. | |
| 5,721,131 A | 2/1998 | Rudolph et al. | |
| 5,723,219 A | 3/1998 | Kolluri et al. | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,783,657 A | 7/1998 | Pavlin et al. | |
| 5,788,979 A * | 8/1998 | Alt et al. | 424/426 |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,857,998 A | 1/1999 | Barry | |
| 5,858,746 A | 1/1999 | Hubbell et al. | |
| 5,865,814 A | 2/1999 | Tuch | |
| 5,869,127 A | 2/1999 | Zhong | |
| 5,871,437 A * | 2/1999 | Alt | 600/3 |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,204,245 B1 * | 3/2001 | Siegel et al. | 514/11 |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |

(56) References Cited

U.S. PATENT DOCUMENTS

| | | |
|---|---|---|
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossainy et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 6,908,624 B2 * | 6/2005 | Hossainy et al. .............. 424/424 |
| 6,939,376 B2 * | 9/2005 | Shulze et al. ................ 623/1.42 |
| 7,217,286 B2 | 5/2007 | Falotico et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 * | 12/2002 | Roorda et al. ................ 604/523 |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 * | 3/2003 | Falotico et al. .............. 623/1.42 |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0108588 A1 * | 6/2003 | Chen et al. .................... 424/423 |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0203915 A1 * | 10/2003 | Fang et al. ................ 514/253.01 |
| 2003/0203991 A1 * | 10/2003 | Schottman et al. ........... 523/334 |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 * | 5/2004 | Hossainy et al. .............. 424/423 |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0037052 A1 | 2/2005 | Udipi et al. |

(56) References Cited

U.S. PATENT DOCUMENTS

| | | |
|---|---|---|
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2006/0014720 A1 | 1/2006 | Hossainy et al. |
| 2006/0105019 A1 | 5/2006 | Stewart et al. |
| 2006/0269586 A1 | 11/2006 | Pacetti |
| 2007/0093617 A1 | 4/2007 | DesNoyer et al. |
| 2007/0149724 A1 | 6/2007 | Pacetti et al. |
| 2007/0167602 A1 | 7/2007 | Pacetti et al. |
| 2007/0228345 A1 | 10/2007 | Pacetti |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| EP | 1604697 A1 * | 12/2005 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/56790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2006/014270 | 2/2006 |
| WO | WO 2007/149825 | 12/2007 |
| WO | WO 2008/016528 | 2/2008 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release ,24:119-132 (1993).

Katsarava et al., *Amino Acid-Based Bioanalogous Polymers. Synthesis and Study of Regular Poly(ester amide)s Based on Bis(α-amino

(56) References Cited

OTHER PUBLICATIONS

*acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (p. 1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Suzuki et al., "Stent-Based Delivery of Sirolimus Reduces Neointimal Formation in a Porcine Coronary Model", Circulation, 104: 1188-1193 (2001).

U.S. Appl. No. 11/824,011, filed Jun. 29, 2007, Pacetti et al.
U.S. Appl. No. 11/888,808, filed Aug. 1, 2007, Ding.
U.S. Appl. No. 11/888,940, filed Aug. 3, 2007, Stankus et al.
U.S. Appl. No. 11/982,160, filed Oct. 31, 2007, Lim et al.

\* cited by examiner

ANTI-PROLIFERATIVE AND ANTI-INFLAMMATORY AGENT COMBINATION FOR TREATMENT OF VASCULAR DISORDERS

CROSS-REFERENCE TO RELATED APPLICATIONS

This is continuation of U.S. patent application Ser. No. 10/882,506, filed on Jun. 30, 2004 now abandoned. This is also a continuation-in-part of U.S. patent application Ser. No. 11/089,763, filed on Mar. 25, 2005 now abandoned, which is a continuation-in-part of U.S. patent application Ser. No. 10/320,935, filed on Dec. 16, 2002, allowed as U.S. Pat. No. 6,908,624 B2.

BACKGROUND OF THE INVENTION

1. Field of the Invention

This invention generally relates to a drug combination including an anti-proliferative drug such as everolimus and an anti-inflammatory agent such as clobetasol for the treatment of a disorder such as restenosis and vulnerable plaque.

2. Description of the Background

Plaques have been associated with stenosis and restenosis. While treatments of plaque-induced stenosis and restenosis have advanced significantly over the last few decades, the morbidity and mortality associated with vascular plaques have remained significant. Recent work suggests that plaque may generally fall into one of two different general types: standard stenotic plaques and vulnerable plaques. Stenotic plaque, which is sometimes referred to as thrombosis-resistant plaque, can generally be treated effectively by the known intravascular lumen opening techniques. Although plaques induce stenoses, these atherosclerotic plaques themselves are often a benign and are an effectively treatable disease.

Unfortunately, as plaque matures, narrowing of a blood vessel by a proliferation of smooth muscle cells, matrix synthesis, and lipid accumulation may result in formation of a plaque which is quite different than a standard stenotic plaque. Such atherosclerotic plaque becomes thrombosis-prone, and can be highly dangerous. This thrombosis-prone or vulnerable plaque may be a frequent cause of acute coronary syndrome.

While the known procedures for treating plaque have gained wide acceptance and shown good efficacy for treatment of standard stenotic plaques, they may be ineffective (and possibly dangerous) when thrombotic conditions are superimposed on atherosclerotic plaques. Specifically, mechanical stresses caused by primary treatments like percutaneous transluminal intervention (PTI), such as stenting, may actually trigger release of fluids and/or solids from a vulnerable plaque into the blood stream, thereby potentially causing a coronary thrombotic occlusion. For example, rupture of the fibrous cap that overlies the thrombogenic necrotic core is presently believed to play an important role in acute ischemic events, such as stroke, transient ischemic attack, myocardial infarction, and unstable angina (Virmani R, et al. Arterioscler Thromb Vasc Biol. 20: 1262-1275 (2000)). There is evidence that fibrous cap can be ruptured during stent deployment. Human data from various sources have indicated that lipid rich and/or positively remodeled and/or echolucent lesions in sysmptomatic coronary atherosclerosis have higher likelihood for restenosis (See, for example, J. Am. Coll. Cardiol. 21(2):298-307 (1993); Am. J. Cardiol. 89(5):505 (2002); Circ. 94(12):3098-102 (1996)). Therefore, there is a need for the treatment of vulnerable plaques and restenosis.

The embodiments of the present invention address these and other needs.

SUMMARY OF THE INVENTION

Described herein are a drug-delivery system and the method of using the drug-delivery system. The drug-delivery system has two or more drugs for treating a vascular disorder or a related disorder. The drugs can be a combination of at least one anti-proliferative agent, at least one anti-inflammatory agent, and optionally a third bioactive agent. In one embodiment, the anti-proliferative agent can be a drug such as everolimus, and the anti-inflammatory agent can be a drug such as clobetasol.

Methods of treating or preventing vascular disorders such as restenosis and vulnerable plaque are also disclosed by administering to the patient a combination of at least one anti-proliferative agent, at least one anti-inflammatory agent, and optionally a third bioactive agent. The mode of delivery can be local or systemic.

DETAILED DESCRIPTION

Anti-proliferative Agents and Anti-inflammatory Agents

Figure 1:
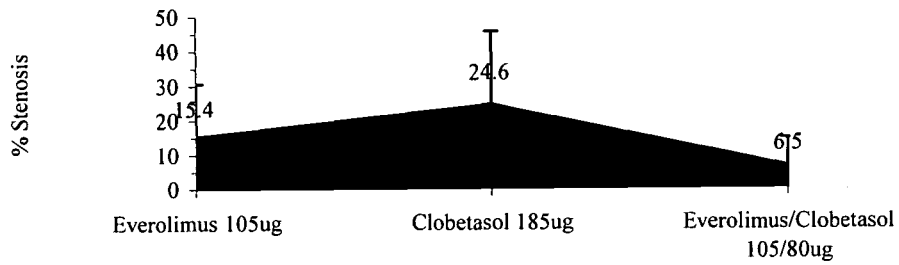
FIG. 1 shows the results of 28 day quantitative coronary angioplasty (QCA) of a porcine implant study on drug-delivery systems described herein.

In accordance with one embodiment, described herein are a drug-delivery system and the method of using the drug-delivery system. The term "treatment" includes prevention, reduction, delay or elimination of the vascular disorder. In some embodiments, treatment also includes repairing damage caused by the dirorder and/or the mechanical intervention. The drug-delivery system has two or more drugs for treating a vascular disorder or a related disorder. The drugs can be a combination of at least one anti-proliferative agent, at least one anti-inflammatory agent, and optionally a third bioactive agent.

In one embodiment, the composition described herein includes an effective amount of at least one anti-inflammatory agent and an effective amount of an anti-proliferative agent. In another embodiment, the composition described herein includes an effective amount of an agent which is effective both as an anti-inflammatory agent and as an anti-proliferative agent.

In some embodiments, the anti-proliferative agent can be everolimus (available under the trade name Certican™, Novartis Pharma AG, Germany), and the anti-inflammatory agent can be clobetasol (available under the trade name Temovate™, Glaxosmithkline, UK).

The anti-proliferative agent and the anti-inflammatory agent can be in the form of a coating with and/or without a polymer matrix on a medical device or at elast one of the agents can be administered in a separate dose form such as bolus dose of a free drug, optionally with fluoroscopic dye, or bolus dose of a gel encapsulating a drug. The drug-delivery system or composition may further include a third agent such as a high-density lipoproptein mimetic (HDL-mimetic). For example, an anti-inflammatory agent such as clobetasol can be delivered along with the catheter based delivery of a HDL-mimetic while everolimus is administered by a stent.

The drug-delivery system or composition disclosed herein can be used to treat or prevent a disorder such as thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

Inflammation in Stenting a Vessel

A common disorder in association with mechanical modification of a vessel, such as by a balloon or stenting, is restenosis. A number of cellular mechanisms have been proposed that lead to restenosis of a vessel. Two of these mechanisms are (1) the migration and proliferation of smooth muscle cells to and at the site of injury, and (2) the acute and chronic inflammatory response to injury and foreign body presence.

Inflammation is a defensive, biological response to injury, infection or an abrupt change in tissue homeostasis. Inflammation can occur anywhere in the body, and most of the time is confined to that part of the body. Well-known indicators of inflammation are pain, redness, warmth, swelling, and loss of function. In nature, inflammatory responses are designed to destroy, dilute and isolate injurious agents and then lead to recovery and repair of the affected tissue. The intensity of an inflammatory response can vary from one that is self-limiting, which requires minor therapeutic intervention, to one that is life threatening, which requires intense intervention. One drawback of the inflammatory process is its ability to become progressive, meaning tissue damage continues after the stimulus is neutralized or removed.

Vascular inflammation is the first stage of the inflammatory response, developing after the initial contact with the stimulus and continuing sometimes for several days. The presence of a stimulatory agent in the blood or in the tissue triggers the body's response through endothelial cells. The endothelial cell layer is the innermost layer of larger vessels and the only cell layer of the smallest vessels, the capillaries. Endothelial cells produce substances called chemokines that attract neutrophils and other white blood cells to the site of injury. Within the site, neutrophils and endothelium relay information back and forth across cell membranes through presentation of adhesion molecules and cytokines. Cellular cross-talk promotes physical interaction between the "inflamed" neutrophil and the "inflamed" endothelium.

Another important pathological feature of vascular inflammation is endothelial cell swelling. This action reduces the functional vessel diameter such that the speed of blood flow falls significantly and the vessel becomes congested. When these conditions predominate, inflamed neutrophils are induced to plug the vessel. As a result, endothelial cells lose their tight connections allowing neutrophils to transmigrate into the surrounding tissue.

Within hours of the initial stimulus, neutrophils begin to enter the tissue and may continue transmigration for many days. The appearance of inflammatory cells in the surrounding tissue marks the beginning of tissue damage. In some inflammatory conditions, tissue damage is caused by direct injury of the vessels and amplified by the subsequent recruitment of neutrophils into the tissue.

Activated by local mediators, neutrophils and tissue macrophages are triggered to release agents that destroy toxins and clean up dead cells in the area. Unfortunately, these same agents also cause collateral damage to healthy cells, which further extends the borders of the initial tissue destruction.

Tissue repair is the third and final stage of inflammation. It may take several days for tissue destruction to reach full intensity before tapering off. Until then, the tissue repair process that consists of growth of new blood vessels and entry of monocytes to clean up the debris is delayed. Fibroblasts also enter the local tissue to replace the extracellular matrix and collagen. The process of tissue repair is stringently controlled within the tissue site. If the process becomes dysregulated, inappropriate tissue repair will lead to excessive scarring. Depending on the tissue and the intensity/duration of the inflammatory condition, the amount of scarring can be significant.

An example of disorders that vessel inflammation is involved is vulnerable plaque (VP) rupture. Previous studies have demonstrated that inflammation promotes proliferation at sites of balloon angioplasty and stent placement in pigs (Kornowski, et al., Coron Artery Dis. 12(6):513-5 (2001)). Since sites of vulnerable plaque have a higher density of macrophages and lymphocytes than other types of atherosclerotic lesions, it is expected that these sites, when stented, will produce elevated amounts of the cytokines (IL-1, TNF-alpha) that promote smooth muscle cell proliferation.

Another example of disorders that vessel inflammation is involved is diabetes. Studies have shown that patients with type-2 diabetes have higher rates of restenosis than the general population. The diabetic patient is in pro-inflammatory state that can amplify restenosis because diabetic lesions contain a large number of inflammatory cells (e.g., macrophages, lymphocytes, etc.).

Anti-Proliferative Agents

Any drugs having anti-proliferative effects can be used in the present invention. The anti-proliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, prodrugs thereof, co-drugs thereof, and combinations thereof.

In one embodiment, the anti-proliferative agent is everolimus. Everolimus acts by first binding to FKBP12 to form a complex (Neuhaus, P., et al., Liver Transpl. 2001 7(6):473-84 (2001) (Review)). The everolimus/FKBP12 complex then binds to mTOR and blocks its activity (Id.). By blocking mTOR activity, cells are unable to pass through G1 of the cell cycle and as a result, proliferation is inhibited. mTOR inhibition has also been shown to inhibit vascular smooth muscle migration.

Anti-inflammatory Agents

Any drugs having anti-inflammatory effects can be used in the present invention. The anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

In one embodiment, the anti-inflammatory agent is clobetasol. Clobetasol is a corticosteroid that binds to corticosteroid receptors, a class of nuclear receptor. The binding of clobetasol to the corticosteroid receptor subsequently alters gene expression in such a way that inflammation is inhibited. For example, corticosteroids inhibit the activation of NFkB, the nuclear factor that is responsible for changes in gene expression that promote inflammation. The reduction in inflammation may also inhibit the mechanisms that promote small muscle cell (SMC) hyper proliferation. This is shown in that dexamethasone, a less potent glucocorticoid as compared to clobetasol, reduces the production of PGDF and thus has anti-proliferative properties. Clobetasol acts through similar pathways and is more potent than dexamethasone.

Dosage

The dosage or concentration of the anti-proliferative and anti-inflammatory agents required to produce a favorable therapeutic effect should be less than the level at which the bioactive agent produces toxic effects and greater than the level at which non-therapeutic results are obtained. The dosage or concentration of the agents required can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies.

In one embodiment, the bioactive agents can be incorporated into polymeric coating in a percent loading of between about 0.01% and less than about 100% by weight, more preferably between about 5% and about 50% by weight of the total drug-load that includes greater than about 0% to about 100% of the anti-proliferative agent and less than about 100% to greater than about 0% of the anti-inflammatory agent. The relative amount of the anti-proliferative agent and anti-inflammatory agent can be determined by the type of lesions to be treated. For example, where everolimus is used as the anti-proliferative agent and clobetasol is used as the anti-inflammatory agent, the relative amount of everolimus and clobetasol can be varied for different types of lesions, that is, the relative amount of everolimus can be higher for more proliferative lesions, and on the other hand, the relative amount of clobetasol can be higher for more inflammatory lesions.

Other Bioactive Agents

In some embodiments, other agents can be used in combination with the anti-proliferative agent and the anti-inflammatory agents. These bioactive agents can be any agent which is a therapeutic, prophylactic, or diagnostic agent. These agents can also have anti-proliferative and/or anti-inflammmatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

Delivery Formulations

The composition comprising both anti-proliferative agent and the anti-inflammatory agent can be formulated into any formulation suitable for delivery by any mode of delivery. For example, the composition can be formed into a coating on an implantable medical device to provide controlled release of the anti-proliferative agent and the anti-inflammatory agent. The composition can also be formulated into other suitable formulations for example, bolus dose of free drug, optionally with a fluoroscopic dye, bolus dose of gel-encapsulated drug.

The gel can be formed of a gel-forming material or polymer such as hyaluronic acid, carboxymethyl cellulose, pectin, hydroxypropyl methylcellulose, hydroxypropyl cellulose, methylcellulose, sodium carboxymethylcellulose, hydroxyethylcellulose, polyethylene oxide, acacia, tragacanth, guar gum, xanthan gum, locust bean gum, Carbopol™ acidic carboxy polymer, polycarbophil, polyethylene oxide, poly(hydroxyalkyl methacrylate), poly(electrolyte complexes), poly (vinyl acetate) cross-linked with hydrolyzable bonds, water-swellable N-vinyl lactams polysaccharides, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, hydrophilic colloids such as carboxylmethyl cellulose gum or alginate gum, including both non-crosslinked and crosslinked alginate gums, where the crosslinked alginate gums may be crosslinked with di- or trivalent ions, polyols such as propylene glycol, or other crosslinking agents, Cyanamer™ polyacrylamides, Good-rite™ polyacrylic acid, starch graft copolymers, Aqua-Keeps™ acrylate polymer, ester crosslinked polyglucan, and the like, and combinations thereof. Some of the gel-forming materials are discussed in U.S. patents, U.S. Pat. Nos. 3,640,741, 3,865,108, 3,992,562, 4,002,173, 4,014,335, and 4,207,893. Hydrogels also are discussed in the Handbook of Common Polymers, by Scott and Roff, published by the Chemical Rubber Company, Cleveland, Ohio. For any given gel-forming material or polymer, use of a material with higher average molecular weight provides higher viscosity in aqueous solution of any given concentration. Therefore, using a higher molecular weight generally enables use of a lesser quantity of polymer to accomplish the required retardation of dissolution. In some embodiments, the gel-forming material or polymer can be hydropropyl methylcellulose having 19-24% methoxyl substitution and 7-12% hydroxypropyl substitution and a number average molecular weight of at least 20,000. Such polymers include those sold by Dow Chemical Co. under the tradenames Methocel K4M, Methocel K15M and Methocel K100M.

Modes of Delivery

In one embodiment, the anti-inflammatory drug such as clobetasol is formulated into a bolus dose of free drug with, optionally, a fluoroscopic dye. The anti-proliferative drug such as everolimus can be formulated into a coating composition with a polymeric material and then coated onto an implantable device (e.g., stent). The bolus dose of anti-inflammatory drug is administered first and then the anti-proliferative drug is delivered by release from the implantable device such as a drug-delivery stent. The composition may further include a third agent such as a HDL (high density lipoprotein)-mimic as described in U.S. Pat. No. 6,367,479. Alternatively, HDL-mimic can be delivered by the stent.

In another embodiment, the anti-inflammatory drug such as clobetasol is formulated into a bolus dose of gel. The anti-proliferative drug such as everolimus can be formulated into a coating composition with a polymeric material and then coated onto an implantable device. The bolus dose of the anti-inflammatory drug is administered first and then the anti-proliferative drug is delivered by release from the implantable device such as a drug-delivery stent.

In a further embodiment, the anti-inflammatory drug and the anti-proliferative drug can be included in a polymeric matrix and then coated onto a medical device such as a stent. The medical device coating can be designed to have a variety of different release parameters for each of the drugs included in the coating. For example, the anti-inflammatory can have one or a combination of release profiles that include a pulse release, fast or burst release, and a sustained release. Similarly, the anti-proliferative drug can have one or a combination of release profiles that include a pulse release, fast or burst release, and a sustained release from the stent. In some embodiments, the combination can be delivered simultaneously or at least during the drug treatment period there is at lease some overlap between the release of the drugs. In some embodiments, the anti-inflammatory can be completely released prior to the. release to the anti-proliferative or can be partially released with some or significant overlap between the release of both drugs. "Pulse release" generally refers to a release profile of a drug that features a sudden surge of the release rate of the drug. The release rate surge of the drug would then disappear within a period. A more detailed definition of the term can be found in Encyclopedia of Controlled Drug Delivery, Edith Mathiowitz, Ed., Culinary and Hospitality Industry Publications Services.

As used herein, the term "fast release" in one embodiment refers to a release profile of a drug that features a release rate in the range between about 15 to about 40 µg per day for a 18 mm stent, about 10 µg to about 27 µg per day for a 13 mm stent, and about 6.7 µg to about 17.2 µg per day for a 8 mm stent. Equivalent profiles can be derived by one having ordinary skill in the art for stents having other sizes. In another embodiment, the term "fast release" refers to an approximately 20% release in 24 hours of a drug. The term "fast release" is used interchangeably with the term "burst release."

As used herein, the term "sustained release" generally refers to a release profile of a drug that can include zero-order release, exponential decay, step-function release or other release profiles that carry over a period of time, for example, ranging from several days to several years. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services).

In one embodiment, at least one of the anti-inflammatory agent (e.g., clobetasol) and anti-proliferative agent (e.g., everolimus) is administered via a stent while the other is administered by other local means of administration or alternatively, the other is administered systemically. In other embodiments, both are administered locally, by means other than a stent, or alternatively systemically. Systemic administration can be accomplished orally or parenterally including intravascularly, rectally, intranasally, intrabronchially, or transdermally. Liquid carriers which are sterile solutions or suspensions can be injected intramuscularly, intraperitoneally, subcutaneously, and intravenously. Rectal administration can be in the form of conventional suppository. For adminsitration by intranasal or intrabronchial inhalation or insufflation, the drug can be formulated into an aqueous or partially aqueous solution, which can then be utilized in the form of an aerosol. The drug can be administered transdermally through the used of a transdermal patch and a carrier that is inert to and mutually compatible with the active component, is non-toxic to the skin, and allows for the delivery of the drug for systemic absorption into the blood stream via the skin. The carrier may take any number of forms such as creams, ointments, pastes, and gels. The creams and ointments may be viscous liquids or semisolid emulsions of either the oil-in-water or water-in-oil type. Pastes made of absorptive powders dispersed in petroleum or hydrophilic petroleum containing the active component may also be suitable. Other devices capable of releasing the drug into the blood stream include semi-permeable membranes covering a reservoir containing the drug, with or without a carrier.

Local administration can be accomplished by a variety of techniques which administer the active component at or near the target site. The following examples of local delivery techniques are provided for illustrative purposes and are not intended to be limiting. Examples include local delivery catheters, site specific carriers, implants, direct application, or direct injection. Local delivery by a catheter allows for the administration of the drug directly to the target site.

Local delivery by site specific carriers is conducted by attaching the drug to a carrier which will direct or link the drug to the target cells. Examples of this delivery technique include the use of carrier such as a protein ligand, a monoclonal antibody or a membrane anchored linker.

Local delivery by an implant (other than a stent) is the placement of a matrix carrying the drug at the site. The matrix can release the active component by, for example, diffusion, degradation, chemical reaction, solvent activators, etc. One example of local delivery by an implant can include direct injection of vesicles or micro-particles. These micro-particles may be composed of substances such as proteins, lipids, carbohydrates or synthetic polymers. The micro-particles can have the drug impregnated therein and/or coated thereon. Application via implants is not limited to the above described routes and other techniques such as grafts, micropumps or application of a fibrin glue or hydrogel containing the active component around the exterior of a designated region of the vessel can also be implemented by one of ordinary skill in the art.

Local delivery by direct injection describes injecting a liquid carrier containing the drug directly into the site. The liquid carrier should be inert to and mutually compatible with the drug. The component can be in true solution or suspended in fine particles in the carrier. A suitable example of an inert carrier includes a sterile saline solution.

Biocompatible Polymers

Any biocompatible polymers can be used to form a coating on a stent or to provide a drug delivery particle with the anti-proliferative drug and/or anti-inflammatory drug. Such biocompatible, bioabsorbable polymers include, but not limited to, poly(ester amide), poly(ester amide) that may contain alkyl groups, amino acid groups, or poly(ethylene glycol) (PEG) groups, polyethylene glycol (PEG), polylakanoates (PHA), poly(2-hydroxyalkanoates), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalknaote) such as poly(4-hydroxybutyrate), poly(4-hydroxyvalerate), poly(4-hydroxyhexanote), poly(4-hydroxyheptanoate), poly(4-hydroxyoctanoate) and copolymers comprising any of the 3-hydroxyalkanoate or 4-hydroxyalkanoate monomers described herein or blends thereof, polyesters, poly(D,L-lactide), poly(L-lactide), polyglycolide, poly(D,L-lactide-co-glycolide), polycaprolactone, poly(D,L-lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(phosphoesters), polyphosphazenes, poly(amino acids), polysaccharides, collagen, chitosan, alginate, polyethers, polyamides, polyurethanes, polyalkylenes, polyalkylene oxides, polyethylene oxide, polypropylene oxide, polyethylene glycol (PEG), PHA-PEG, polyvinylpyrrolidone (PVP), alkylene vinyl acetate copolymers such as ethylene vinyl acetate (EVA), alkylene vinyl alcohol copolymers such as ethylene vinyl alcohol (EVOH or EVAL), poly(n-butyl methacrylate) (PBMA), SOLEF™ polymers such as poly(vinylidene fluoride-co-hexafluoropropene) (PVDF-co-HFP) and poly(vinylidene fluoride) (PVDF) and combinations thereof.

Method of Coating A Device

The coating described herein can be formed by spray coating or any other coating process available in the art. Generally, the coating involves dissolving or suspending the composition, or one or more components thereof, in a solvent or solvent mixture to form a solution, suspension, or dispersion of the composition or one or more components thereof, applying the solution or suspension to an implantable device, and removing the solvent or solvent mixture to form a coating or a layer of coating. Suspensions or dispersions of the composition described herein can be in the form of latex or emulsion of microparticles having a size between 1 nanometer and 100 microns, preferably between 1 nanometer and 10 microns. Heat and/or pressure treatment can be applied to any of the steps involved herein. In addition, if desirable, the coating described here can be subjected to further heat and/or pressure treatment. Some additional exemplary processes of coating an implantable device that may be used are described in, for example, Lambert T L, et al. Circulation, 1994, 90: 1003-1011; Hwang C W, et al. Circulation, 2001, 104: 600-605; Van der Giessen W J, et al. Circulation, 1996, 94: 1690-1697; Lincoff A M, et al. J Am Coll Cardiol 1997, 29: 808-816; Grube E. et al, J American College Cardiology Meeting, Mar. 6, 2002, ACCIS2002, poster 1174-15; Grube E, et al, Circulation, 2003, 107: 1, 38-42; Bullesfeld L, et al. Z Kardiol, 2003, 92: 10, 825-832; and Tanabe K, et al. Circulation 2003, 107: 4, 559-64.

As used herein, the term "solvent" refers to a liquid substance or composition that is compatible with the polymer and is capable of dissolving or suspending the polymeric composition or one or more components thereof at a desired concentration. Representative examples of solvents include chloroform, acetone, water (buffered saline), dimethylsulfoxide (DMSO), propylene glycol monomethyl ether (PM,) isopropylalcohol (IPA), n-propyl alcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, 1,1,2-trichloroethane, formamide, hexafluoroisopropanol, 1,1,1-trifluoroethanol, and hexamethyl phosphoramide and a combination thereof.

Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In one embodiment, the implantable device is a stent, which can be degradable stents, biodurable stents, depot stents, and metallic stens such as stents made of stainless steel or nitinol. The stents can be balloon expandable or self expanding.

Method of Use

In accordance with embodiments of the invention, a coating of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device comprising a coating described herein can be used to treat an animal having a condition or disorder that requires a treatment. Such an animal can be treated by, for example, implanting a device described herein in the animal. Preferably, the animal is a human being. Exemplary disorders or conditions that can be treated by the method disclosed herein include, but not limited to, thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

EXAMPLES

The embodiments of the present invention will be illustrated by the following set forth examples. All parameters and data are not to be construed to unduly limit the scope of the embodiments of the invention.

Example 1

Porcine Implant Study

Described in this example is a 28 day porcine implant study that compared the 200 µg/cm² dose Lemans with a clobetasol-only delivery stent, an everolimus-only stent, and an everolimus-clobetasol combination drug delivery stent. The study was performed using three different drug delivery stents, Arm 1, Arm 2, and Arm 3. Arm 1 is Lemans stent (a stent available from Guidant based on PVDF-co-HFP) that included 105 µg everolimus and used as a control. Arm 2 was loaded with 185 µg clobetasol only, with no everolimus. Arm 3 is loaded with 105 µg everolimus and 80 µg clobetasol.

The Arm 1, Arm 2, and Arm 3 stents were implanted in a 30% overstretch model. Nine samples of each Arm stent were implanted, one for each coronary artery. 24 hr Release in porcine serum data were gathered. 3, 7 and 28 day in vivo release data were gathered (from the mammary arteries), as was 28 day quantitative coronary angioplasty (QCA), histology and morphometry.

In this study, 12 mm Vision Small stents (available from Guidant) were used. All drug solutions were sprayed in a 2% Solef™ in acetone/cyclohexanone formulation. All stents had a 100 µg PBMA primer. Table 1 shows the coating design of the stents used in this study.

TABLE 1

| | Coating design | | | | | | |
|---|---|---|---|---|---|---|---|
| | Drug (D) | Polymer (P) | D:P | Drug % | Evererolimus Target (µg) | Clobetasol Target (µg) | Solid Target (µg) |
| Arm 1 | Everolimus | Solef™ | 1:3 | 25.0 | 105 | — | 420 |
| Arm 2 | Clobetasol | Solef™ | 1:4.2 | 19.2 | — | 185 | 962 |
| Arm 3 | Ever & Clob | Solef™ | 1:3.49 | 22.2 | 105 | 80 | 833 |

The release rate data are shown in Table 2. As can be seen from Table 2, a coating based on Solef™ is capable of simultaneous release of both everolimus 10 and clobetasol.

TABLE 2

| | Release rate data | | | | | | | |
|---|---|---|---|---|---|---|---|---|
| Arm | In vivo Day 3 % Clobetasol Release (n = 2) | In vivo Day 7 % Clobetasol Release (n = 3) | In vivo Day 28 % Clobetasol Release (n = 4) | In vitro 24 hr % Clobetasol Release in PS (n = 3) | In vivo Day 3 % Everolimus Release (n = 2) | In vivo Day 7 % Everolimus Release (n = 3) | In vivo Day 28 % Everolimus Release (n = 4) | In vitro 24 hr % Everolimus Release in PS (n = 3) |
| 1 - Everolimus | | | | | 37.6% | 49.3% | 66.7% | 30.0% |
| 2 - Clobetasol | 32.5% | 43.1% | 60.6% | 26.7% | | | | |
| 3 - Everolimus + Clobetasol | 40.9% | 50.2% | 71.9% | 30.1% | 35.1% | 43.6% | 60.4% | 24.8% |

Figure 2:
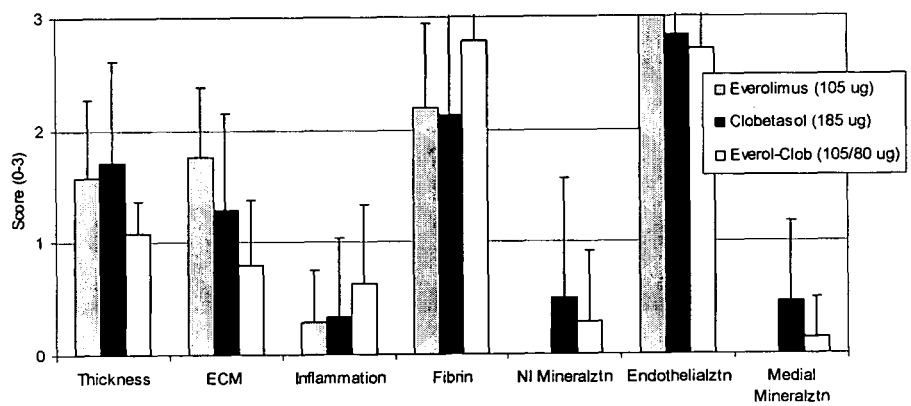
FIG. 2 shows 28 day histology data of a porcine implant study on drug-delivery systems described herein.
Figure 3:
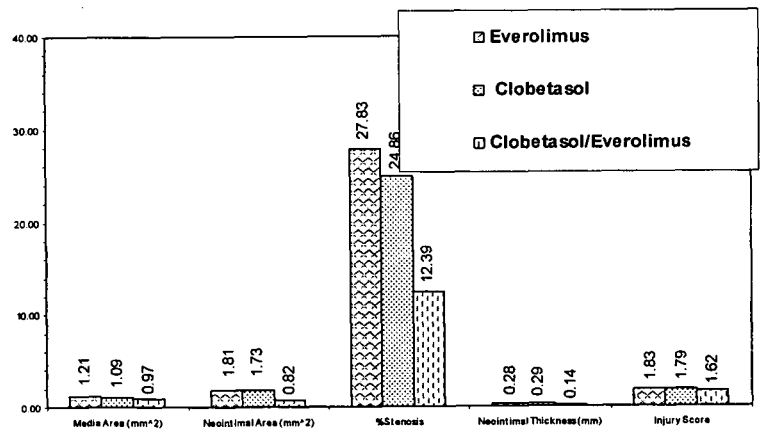
FIG. 3 shows the 28 day morphometry data of a porcine implant study on drug-delivery systems described herein.

The results of 28 day QCA are shown in FIG. 1, the 28 day histology data are in FIG. 2, and the 28 day morphometry data are shown in FIG. 3 and summarized in Table 3 below.

TABLE 3

| | 28 Day morphometry data from FIG. 3 | | | | | | | | | | |
|---|---|---|---|---|---|---|---|---|---|---|---|
| | AVERAGE | | | | | STANDARD DEVIATION | | | | | |
| | Media Area (mm^2) | Neointimal Area (mm^2) | % Stenosis | Neointimal Thickness (mm) | Injury Score | | Media Area (mm^2) | Neointimal Area (mm^2) | % Stenosis | Neointimal Thickness (mm) | Injury Score |
| Everolimus | 1.21 | 1.81 | 27.83 | 0.28 | 1.83 | Everolimus | 0.23 | 0.72 | 13.18 | 0.11 | 0.23 |
| Clobetasol | 1.09 | 1.73 | 24.86 | 0.29 | 1.79 | Clobetasol | 0.18 | 1.57 | 23.27 | 0.23 | 0.22 |
| Clobetasol/ Everolimus | 0.97 | 0.82 | 12.39 | 0.14 | 1.62 | Clobetasol/ Everolimus | 0.18 | 0.39 | 7.54 | 0.04 | 0.29 |

The p values from a t-test of the data from FIG. 3 are summarized in Table 4. A "t-test" returns the probability associated with a Student's t-Test that determines whether two samples are likely to have come from the same two underlying populations that have the same mean. The value returned from the test, "p", is the probability that the two groups of data come from the same population. p Values less than or equal to 0.10 or 0.05 are generally considered significant (Zar, J H. *Biostatistical Analysis*. Englewood Cliffs, N.J.: Prentice-Hall Inc, 1974. pp 101-108).

TABLE 4 p Values from a t-test of the data from FIG. 3

| Arm Comparison | | Media Area | Neointimal Area | % Stenosis | Neointimal Thickness | Injury Score |
|---|---|---|---|---|---|---|
| EVER | COMBO | 0.05 | 0.01 | 0.02 | 0.01 | 0.18 |
| EVER | CLOB | 0.29 | 0.90 | 0.77 | 0.93 | 0.78 |
| COMBO | CLOB | 0.24 | 0.18 | 0.22 | 0.14 | 0.25 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A local drug-delivery system, comprising:
   a polymeric coating which comprises an effective amount of everolimus, and
   an effective amount of clobetasol for the treatment of a vascular disorder or a related disorder,
   wherein the polymeric coating releases clobetasol completely or partially prior to releasing everolimus.

2. The drug-delivery system of claim 1, wherein the drug-delivery system is a stent.

3. The drug-delivery system of claim 1, wherein the vascular disorder or the related disorder is restenosis.

4. The drug-delivery system of claim 1, wherein the vascular disorder or the related disorder is restenosis, progression of atherosclerosis, or a combination thereof.

5. The drug-delivery system of claim 1, wherein the vascular disorder or the related disorder is vulnerable plaque.

6. The drug-delivery system of claim 1, wherein the drug-delivery system is a polymer or a polymeric coating.

7. A method of treating vascular disease, comprising:
   administering locally to a patient in need thereof a combination of
   an effective amount of everolimus, and
   an effective amount of clobetasol by a drug-delivery device,
   wherein clobetasol is released completely or partially prior to releasing everolimus.

8. The method of claim 7, wherein the drug-delivery device is a stent.

9. The method of claim 7, wherein the vascular disease is restenosis, progression of atherosclerosis, or vascular plaque.

* * * * *

UNITED STATES PATENT AND TRADEMARK OFFICE
CERTIFICATE OF CORRECTION

| | | |
|---|---|---|
| PATENT NO. | : 8,586,069 B2 | Page 1 of 1 |
| APPLICATION NO. | : 11/322282 | |
| DATED | : November 19, 2013 | |
| INVENTOR(S) | : Stewart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 867 days.

Signed and Sealed this
Twenty-fourth Day of March, 2015

Michelle K. Lee
*Director of the United States Patent and Trademark Office*